United States Patent
Sumita

(10) Patent No.: US 8,562,860 B2
(45) Date of Patent: Oct. 22, 2013

(54) METHOD FOR ACTIVATING AND STABILIZING DISSOLVED HYDROGEN IN WATER

(75) Inventor: Osao Sumita, Tokyo (JP)

(73) Assignee: Spring Co., Ltd., Tokyo (JP)

( * ) Notice: Subject to any disclaimer, the term of this patent is extended or adjusted under 35 U.S.C. 154(b) by 604 days.

(21) Appl. No.: 12/308,379

(22) PCT Filed: Jul. 5, 2007

(86) PCT No.: PCT/JP2007/063420
§ 371 (c)(1),
(2), (4) Date: Jan. 21, 2009

(87) PCT Pub. No.: WO2008/015867
PCT Pub. Date: Feb. 7, 2008

(65) Prior Publication Data
US 2009/0311342 A1    Dec. 17, 2009

(30) Foreign Application Priority Data

Aug. 4, 2006 (JP) ................ 2006-213475

(51) Int. Cl.
| | | |
|---|---|---|
| C01B 3/00 | (2006.01) | |
| C01B 6/00 | (2006.01) | |
| C06B 23/00 | (2006.01) | |
| C06B 43/00 | (2006.01) | |
| C02F 1/70 | (2006.01) | |
| C09K 3/00 | (2006.01) | |
| B65B 3/00 | (2006.01) | |
| A01N 59/00 | (2006.01) | |
| A01N 59/20 | (2006.01) | |
| A01N 59/16 | (2006.01) | |
| A61K 33/40 | (2006.01) | |
| A61K 33/32 | (2006.01) | |

(52) U.S. Cl.
USPC ...... 252/188.28; 424/400; 424/600; 424/613; 424/630; 424/639; 424/641; 424/643; 424/646; 261/75; 206/0.6

(58) Field of Classification Search
USPC ......... 424/600, 400, 613, 630, 639, 641, 643, 424/646; 252/188, 188.28; 261/75; 206/0.6; 204/263, 265, 266, 282, 283; 205/242, 205/252, 263, 628, 638, 701, 742, 751; 521/26, 27, 28, 38
See application file for complete search history.

(56) References Cited

U.S. PATENT DOCUMENTS 4,332,665 A * 6/1982 Kimoto et al. ............... 204/296
5,616,221 A * 4/1997 Aoki et al. ................... 204/252
(Continued)

FOREIGN PATENT DOCUMENTS

| JP | H10-296262 | 11/1998 |
| JP | H11-077048 | 3/1999 |

(Continued)

OTHER PUBLICATIONS

Linde, "Nitrogen", (2007) http://www.aga.is/international/web/Ig/us/like/gus30.nsf/docbyalias/nav_prod_bulk_n2.*
Linde, "Carbon Dioxide", (2007), http://www.aga.is/international/web/Ig/us/like/gus30.nsf/docbyalias/nav_prod_bulk_co2.*

(Continued)

*Primary Examiner* — Jane C Oswecki
(74) *Attorney, Agent, or Firm* — Manabu Kanesaka

(57) ABSTRACT

A method for activating hydrogen molecules dissolved in water and stabilizing the concentration of the hydrogen molecules is provided. The method for activating and stabilizing hydrogen molecules dissolved in water is characterized by allowing hydrogen ions to coexist with the hydrogen molecules.

16 Claims, 16 Drawing Sheets

Structure of three-chamber type electrolytic cell utilizing cation exchange membrane or anion exchange membrane of vinyl chloride-based and hydrocarbon-based and reaction scheme.

(56) References Cited

U.S. PATENT DOCUMENTS

| | | | |
|---|---|---|---|
| 2005/0170011 A1 | 8/2005 | Yanagihara et al. | |
| 2009/0223974 A1* | 9/2009 | Felius | 220/560.12 |
| 2010/0209529 A1* | 8/2010 | Satoh | 424/600 |

FOREIGN PATENT DOCUMENTS

| | | | |
|---|---|---|---|
| JP | 2002-301483 | | 10/2002 |
| JP | 2002-361250 | | 12/2002 |
| JP | 2003-095915 | | 4/2003 |
| JP | 2005-065620 | | 3/2005 |
| JP | 2005-065620 A * | | 3/2005 |
| JP | 2005-177724 | | 7/2005 |
| JP | 2005-177724 A * | | 7/2005 |
| JP | 2005-342645 | | 12/2005 |
| JP | 2005-342645 A * | | 12/2005 |
| WO | WO 2006003192 A1 * | | 1/2006 |

OTHER PUBLICATIONS

"pH"; (1979) http://en.wikipedia.org/wiki/PH.*

"pH", Wikipedia [online], 1979, [retrieved on Jul. 6, 2012] Retrieved from the Internet<URL: http://en.wikipedia.org/wiki/PH>.*

"Hydrogen", Published online Dec. 20, 2001; [retrieved on Jul. 6, 2012] Kirk-Othmer Encyclopedia of Chemical Technology; vol. 13, p. 759; Retrieved from the Internet: <URL: http://onlinelibrary.wiley.com/doi/10.1002/0471238961.0825041803262116.a01.;pub2/pdf>.*

"Titanium", Wikipedia [online], 2000-2006, [retrieved on Jul. 6, 2012] Retrieved from the Internet: <URL: http://en.wikipedia.org/wiki/Titanium>.*

Linde products, CO2 and N2 compressed gas in containers, [retrieved on Jul. 6, 2012] Retrieved from the Internet: <URL: http://www.aga.is/international/web/Ig/us/like/gus30.nsf/docbyalias/nav_prod_bulk_co2 and n2.*

* cited by examiner

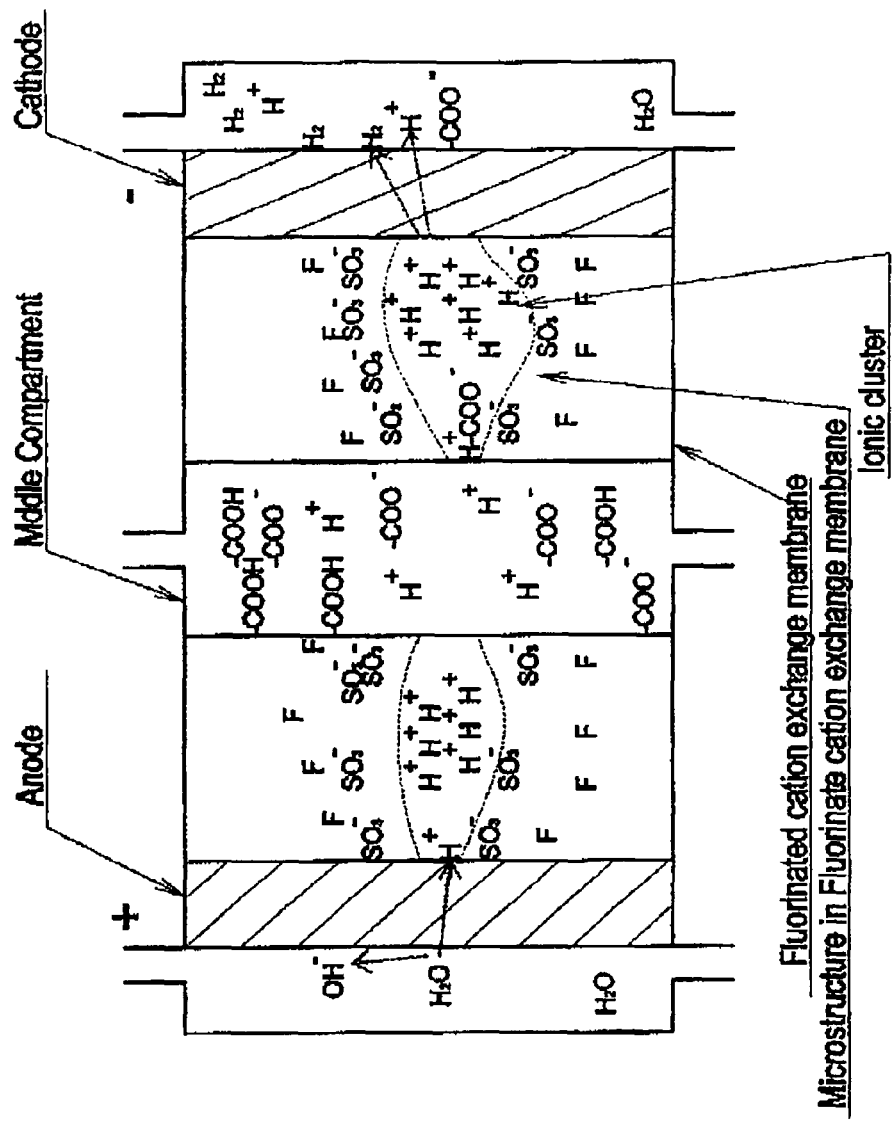
Fig. 1: Structure of three-chamber type electrolytic cell utilizing fluorine-based cation exchange membranes and reaction scheme

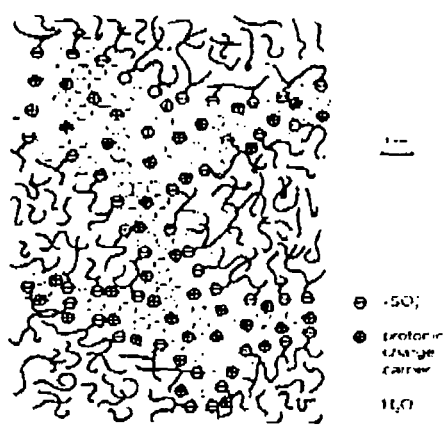
Fig. 2: Microstructure in fluorine-based cation exchange membrane

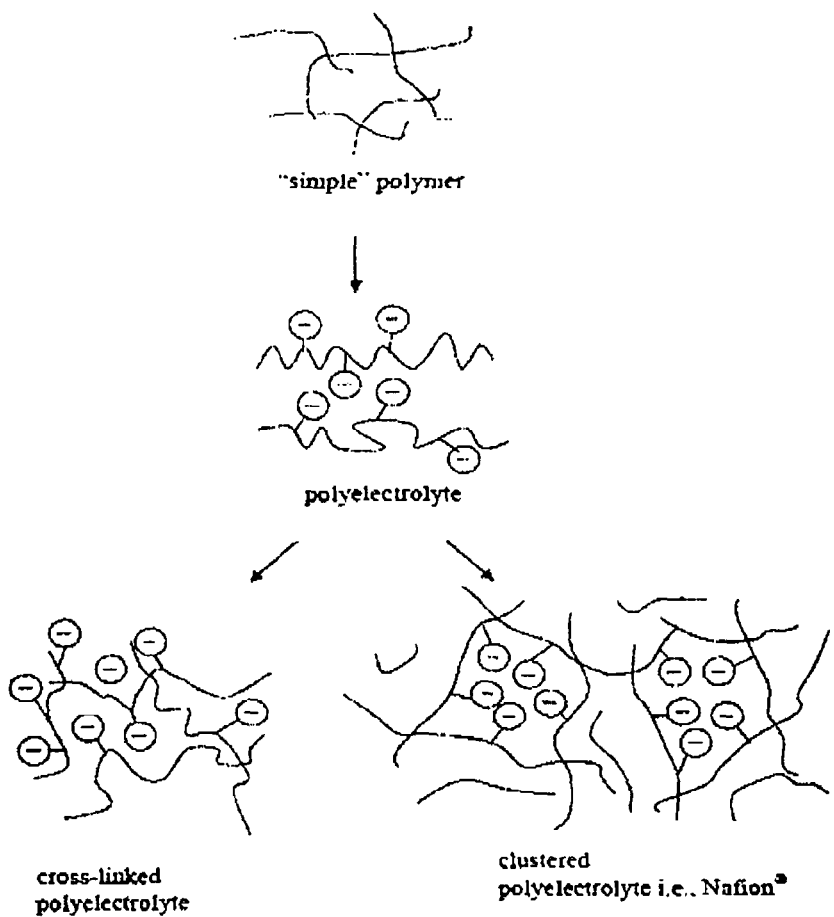
Fig. 3: Arrangement in a cluster form of exchange groups in fluorine-based cation exchange membrane

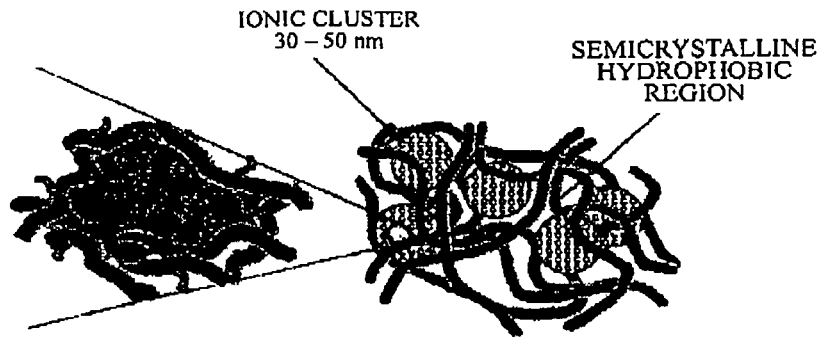
Figure 2-4. Schematic representation of ionic clusters in phase separated domain of Nafion® by Mauritz et.al.
Fig. 4: Formation of cluster ions
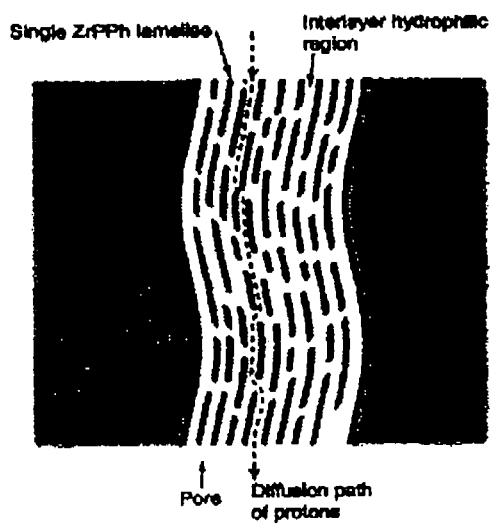
Figure 2.43 A schematic representation of diffusion path of protons through the ZrPPh
Fig. 5: Arrangement of hydrogen ion clusters in ion exchange membrane

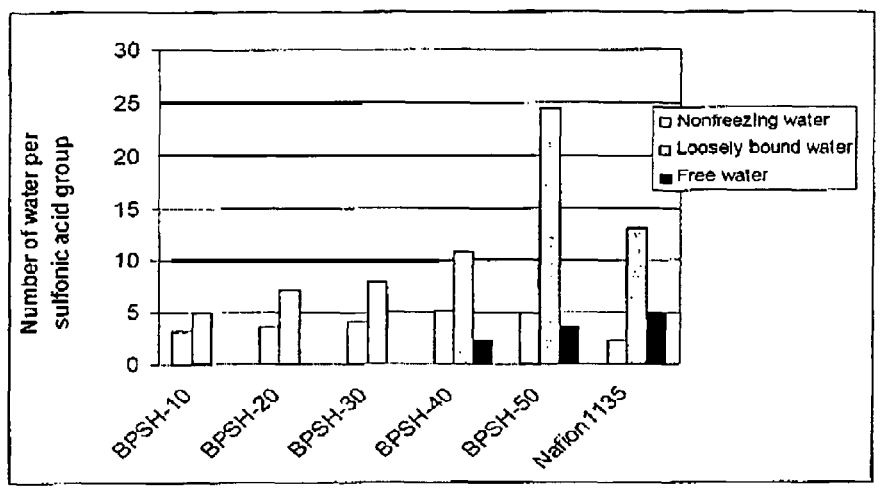
Figure 2.39 Composition of each state of water for BPSH and Nafion™ membranes; No
Fig. 6 : Rate of absorption of water in fluorine-based cation exchange membrane

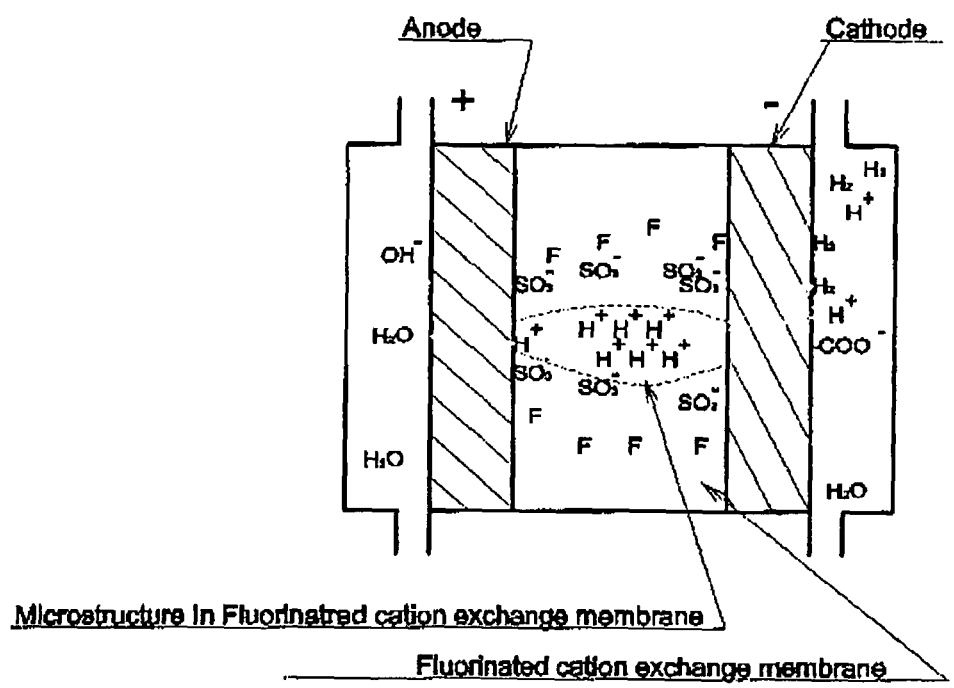
Fig. 7: Basic electrolytic cell structure utilizing fluorine-based ion exchange membrane

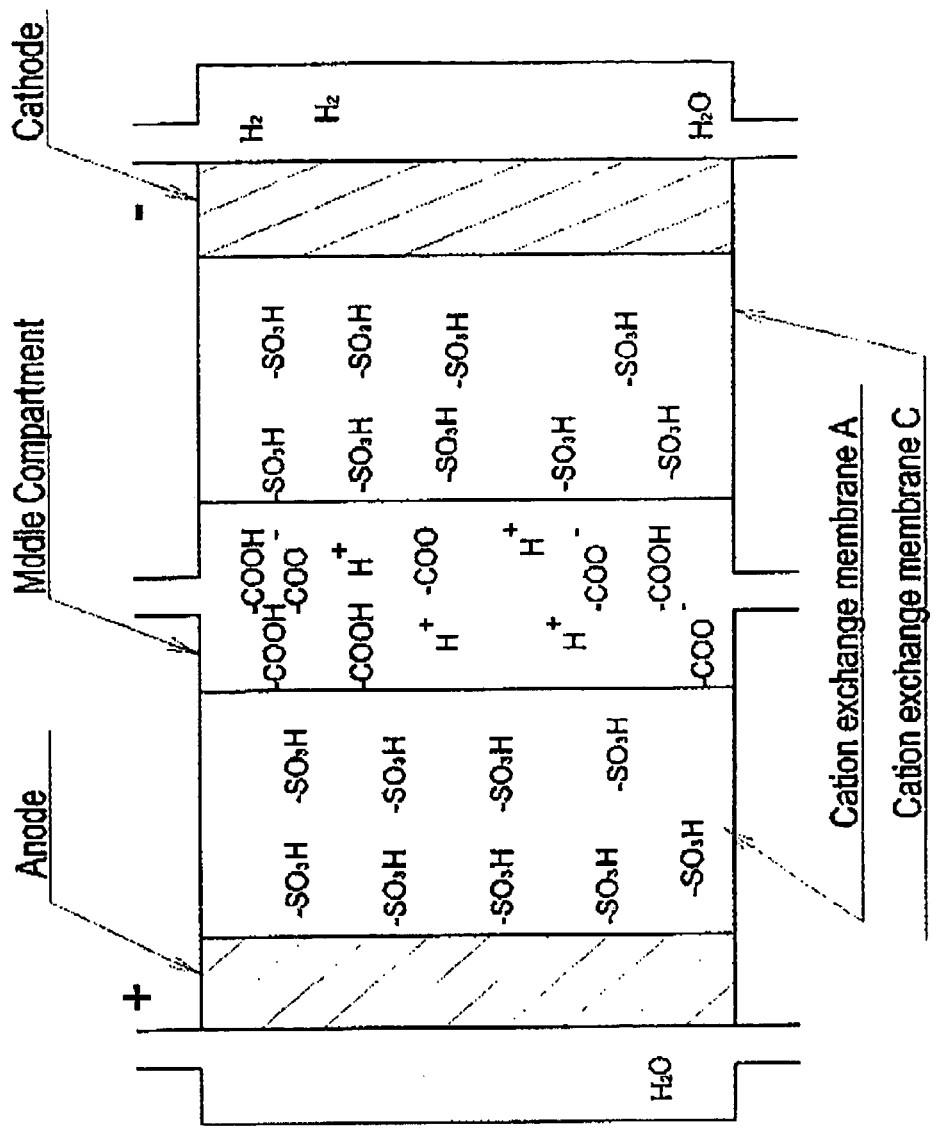
Fig. 8: Structure of three-chamber type electrolytic cell utilizing vinyl chloride-based and hydrocarbon-based cation exchange membranes and reaction scheme

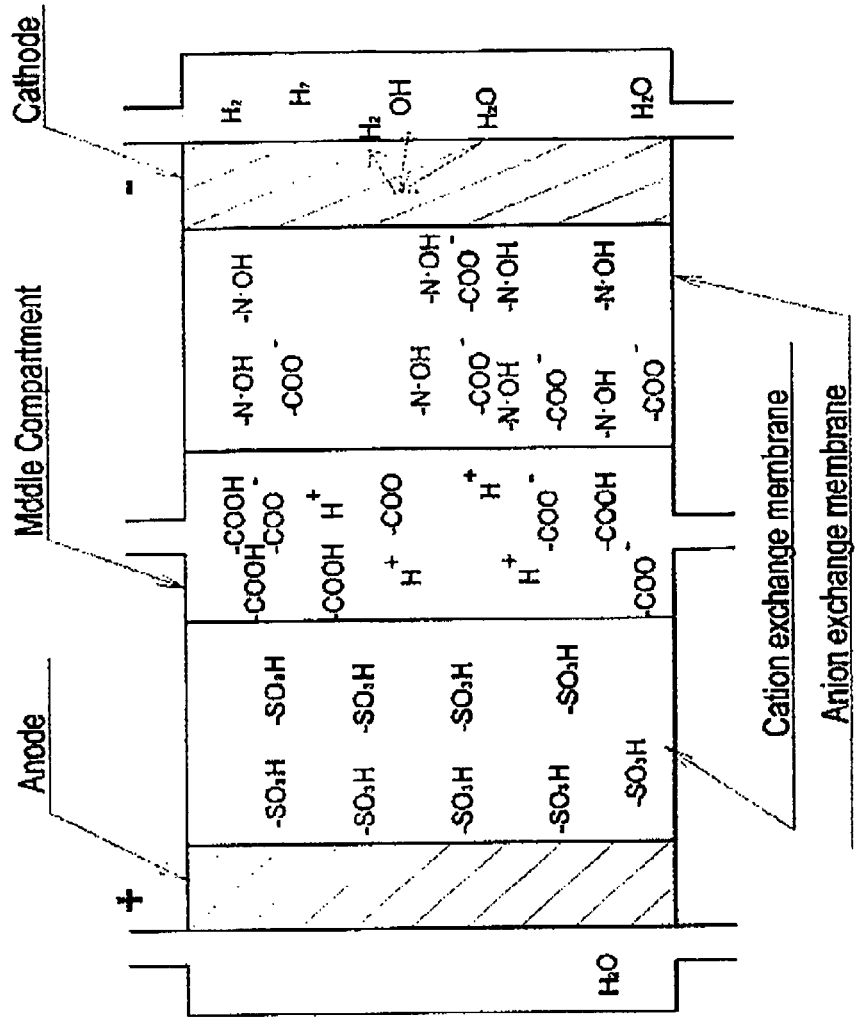
Fig. 9: Structure of three-chamber type electrolytic cell utilizing cation exchange membrane or anion exchange membrane of vinyl chloride-based and hydrocarbon-based and reaction scheme.

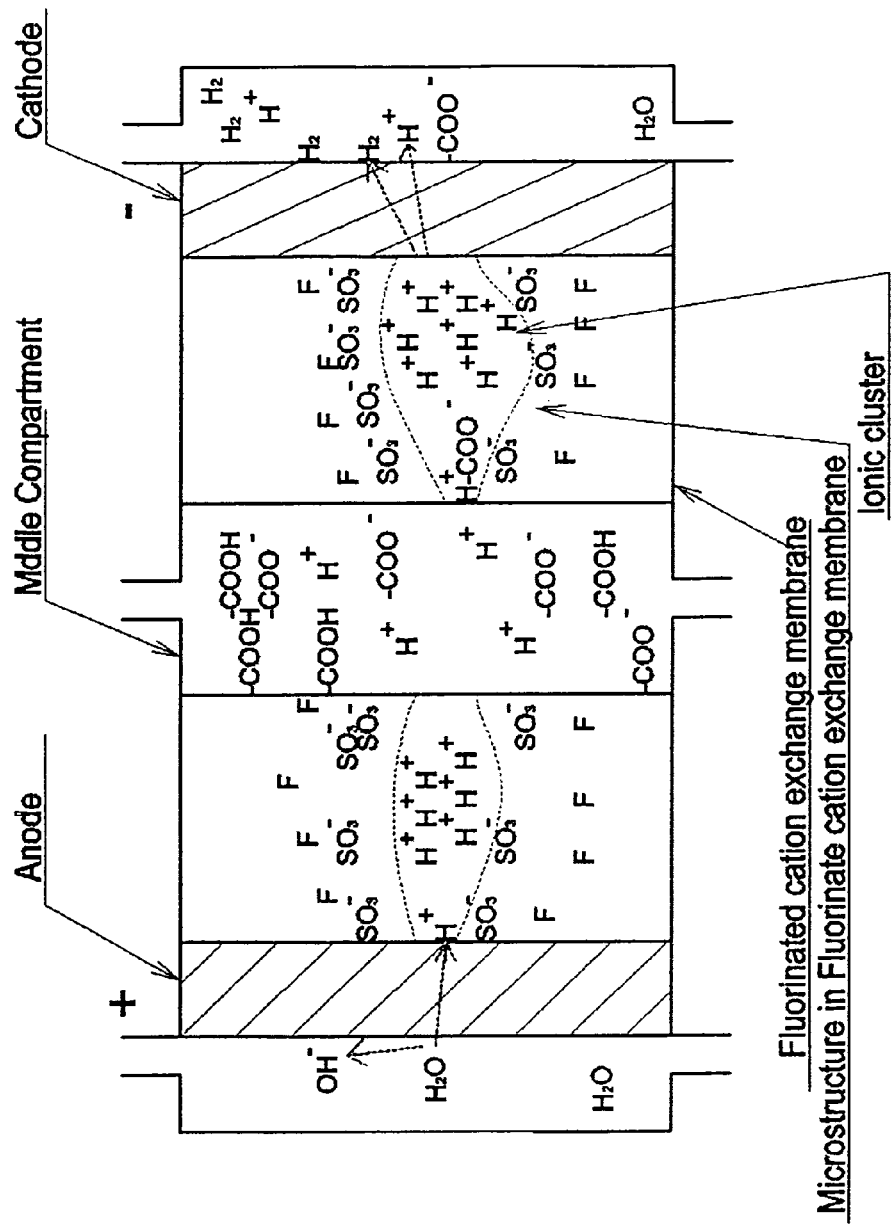
Fig. 10 : Structure of three-chamber type electrolytic cell utilizing fluorine-based cation exchange membranes and reaction scheme

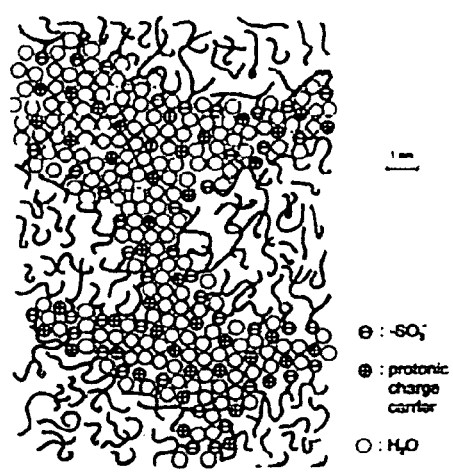
Schematic representation of the microstructure of Nafion® (ref. 20).
Fig. 11 : Microstructure in fluorine-based cation exchange membrane

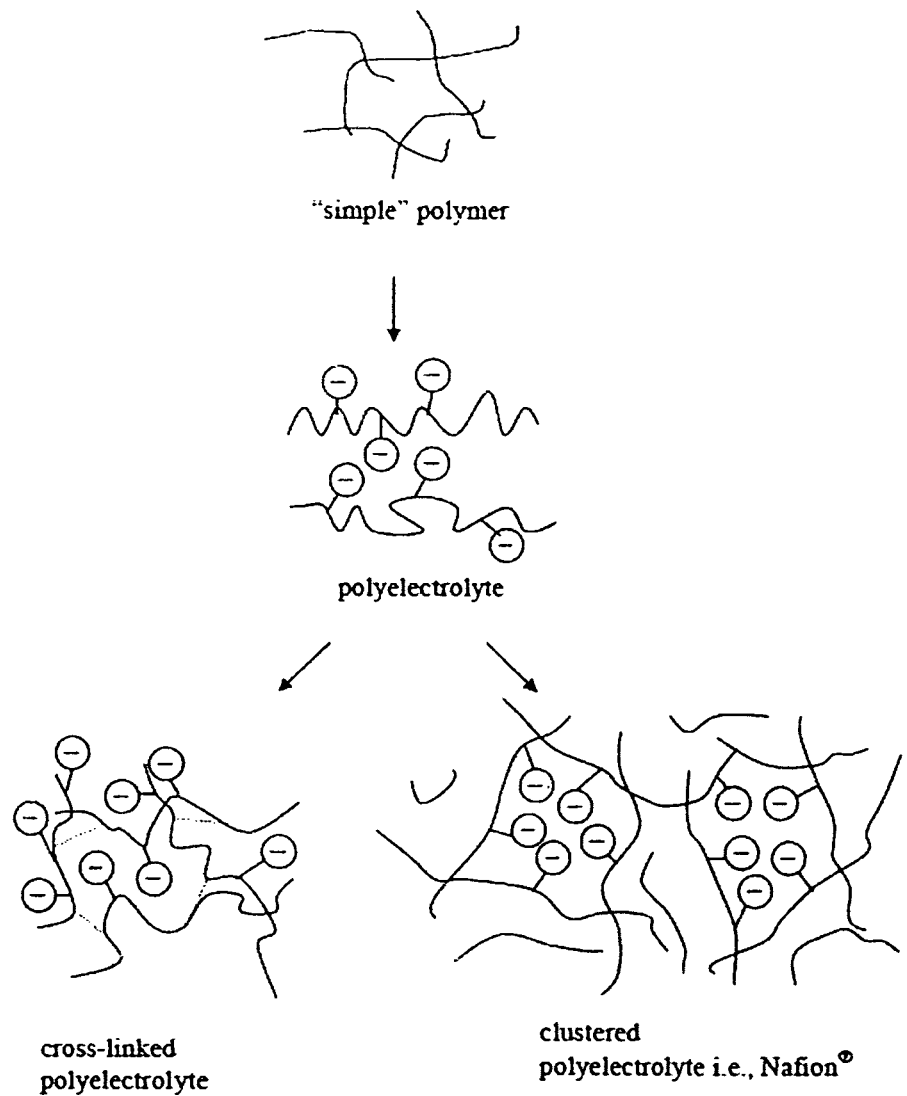
Fig. 12 : Arrangement in a cluster form of exchange groups in fluorine-based cation exchange membrane

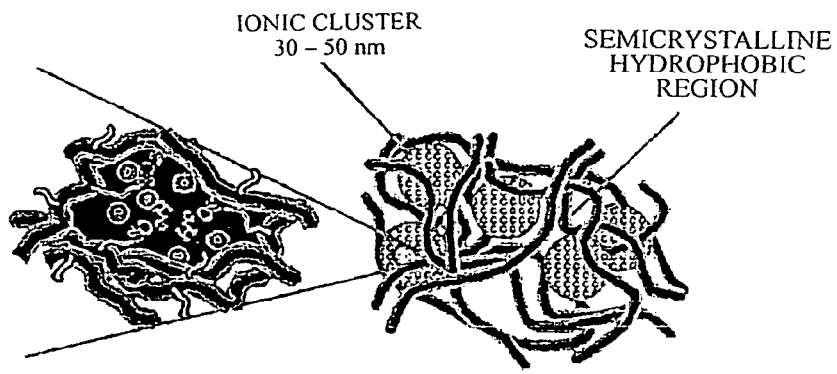
Schematic representation of ionic clusters in phase separated domain of Nafion® by Mauritz et.al.
Fig. 13 : Formation of cluster ions
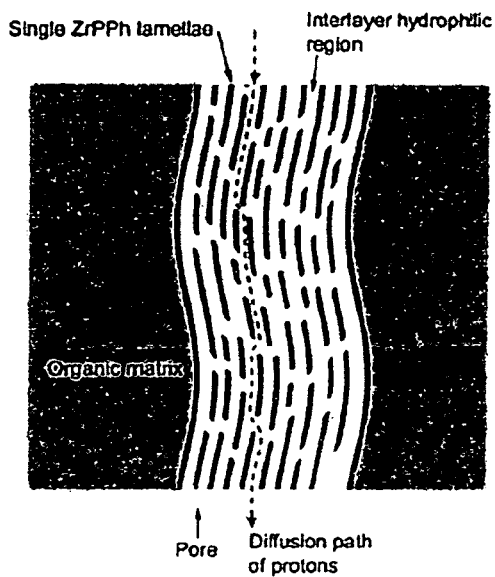
A schematic representation of diffusion path of protons through the ZrPPh
Fig. 14 : Arrangement of hydrogen ion clusters in ion exchange membrane

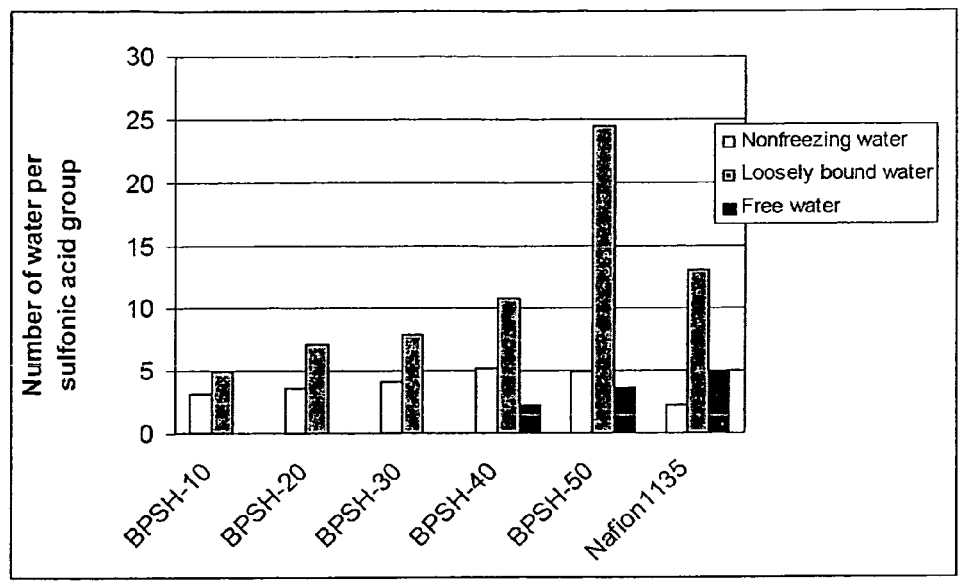
Composition of each state of water for BPSH and Nafion™ membranes; No
Fig. 15 : Rate of absorption of water in fluorine-based cation exchange membrane

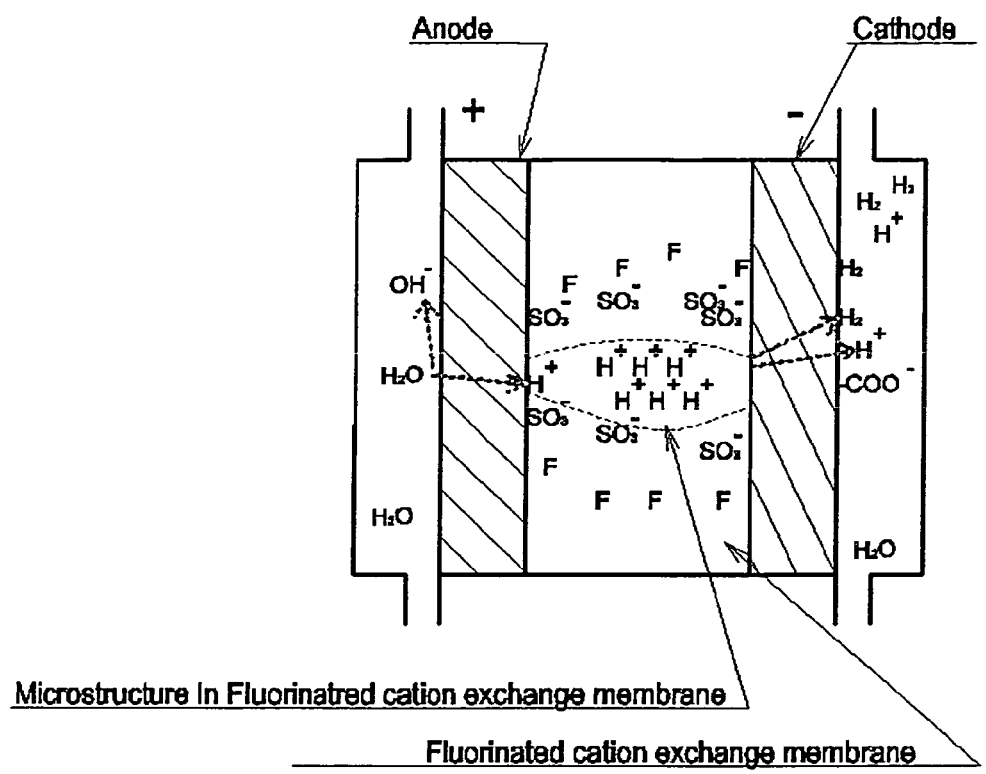
Fig. 16 : Basic electrolytic cell structure utilizing fluorine-based ion exchange membrane

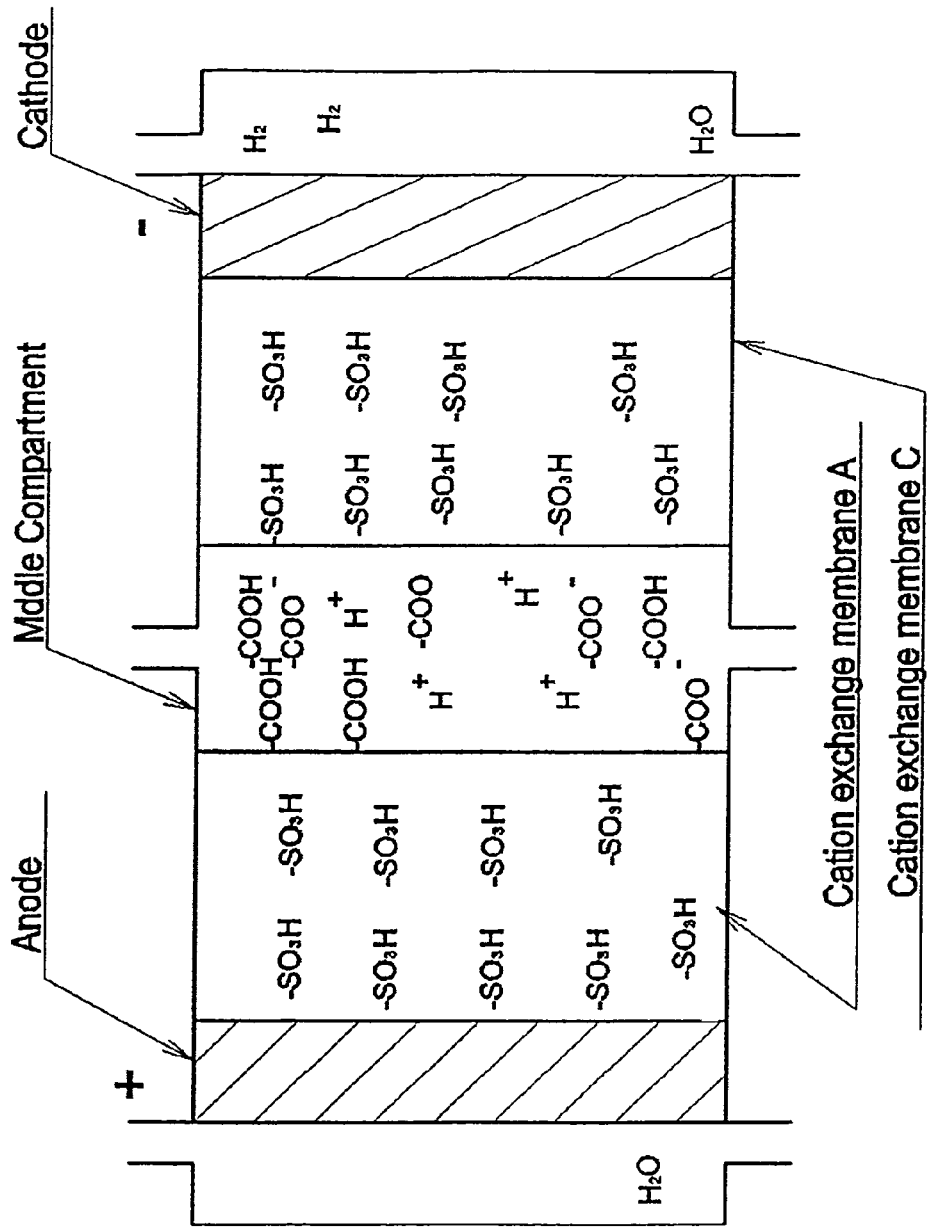
Fig. 17 : Structure of three-chamber type electrolytic cell utilizing vinyl chloride-based and hydrocarbon-based cation exchange membranes and reaction scheme

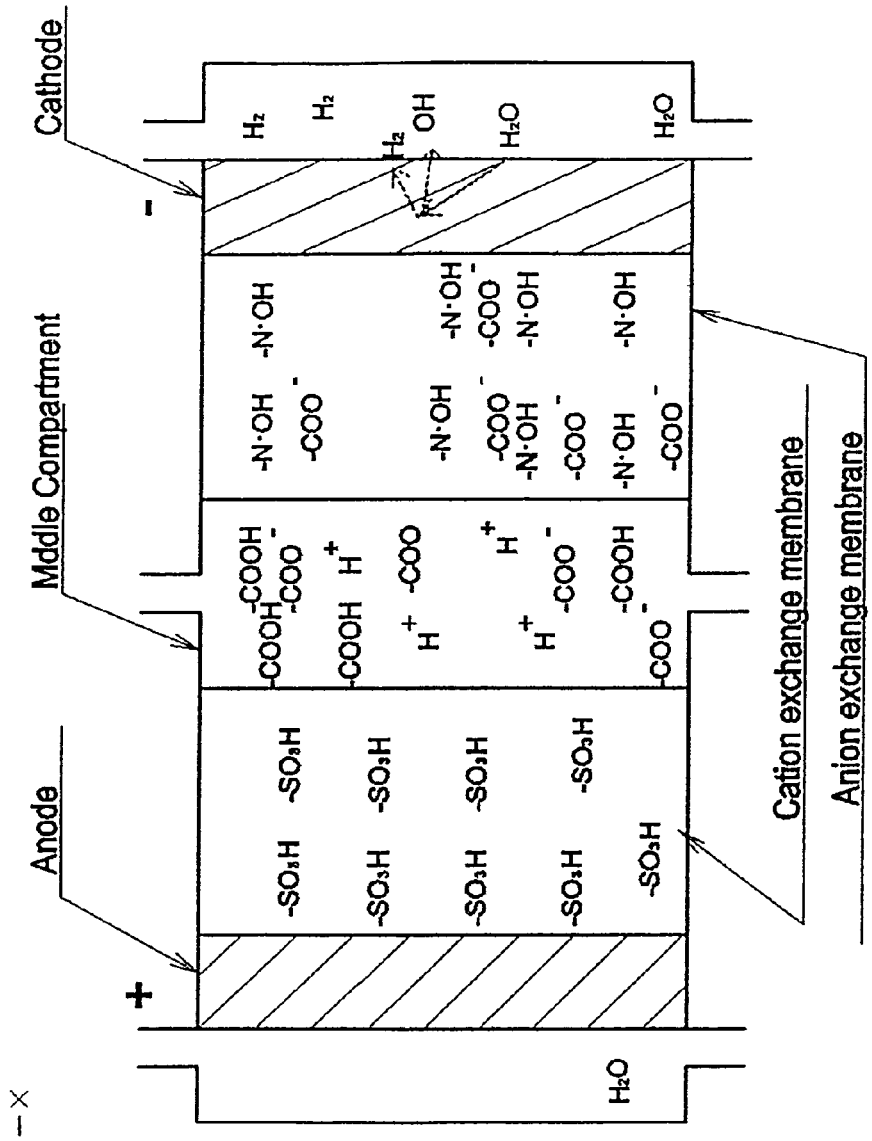
Fig. 18: Structure of three-chamber type electrolytic cell utilizing cation exchange membrane or anion exchange membrane of vinyl chloride-based and hydrocarbon-based and reaction scheme.

METHOD FOR ACTIVATING AND STABILIZING DISSOLVED HYDROGEN IN WATER

CROSS-REFERENCE TO RELATED APPLICATIONS

The present application is National Phase entry of International Application No. PCT/JP2007/063420 filed on Jul. 5, 2007, and claims priority from, Japanese Application No. 2006-213475, filed on Aug. 4, 2006.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION (1) Field of the Invention

The present invention relates to a method for activating and stabilizing dissolved hydrogen in water.

(2) Description of Related Art

The dissolved states of hydrogen molecules in water are broadly categorized into dissolution in molecular form and dissolution in fine gas bubble form. However, hydrogen in molecular form and hydrogen in fine gas bubble form are difficult to distinguish, and it has been reported that the solubility of molecular hydrogen, including small hydrogen gas bubbles, in water is only of the order of several ppm.

The next problem is that dissolved molecular hydrogen is unstable in water and is vaporized rapidly from water, so that the concentration of the dissolved hydrogen decreases. Even when hydrogen gas is dissolved in pure neutral water to the saturation concentration, the concentration of dissolved hydrogen decreases to one-tenth or less in about 2 hours under open conditions. Therefore, to store a solution containing molecular hydrogen dissolved therein, careful consideration must be given to the material for the container and the method for filling the container.

A significant difficulty in utilizing molecular hydrogen is its activity. Generally, hydrogen molecules basically have reducing properties. However, as described in FIG. 1, energy greater than the activation energy is required to allow the reaction to proceed. The activation energy for hydrogen molecules is known to be large, and therefore the reaction rate is small. Accordingly, the reduction reaction is not apparently observed.

Meanwhile, a human ingests organic substances and oxygen in a human body, and energy is produced in the reduction process of ingested oxygen with hydrogen in ingested organic substances to water. However, it has been reported that, in this reduction process of oxygen, about 2% of oxygen is converted to superoxide ($O_2^-$). This superoxide in the body is decomposed by SOD enzyme into hydrogen peroxide ($H_2O_2$) and oxygen (see the following chemical formula (1)).

$$2O_2^- + 2H^+ \rightarrow O_2 + H_2O_2 \tag{1}$$

The produced hydrogen peroxide is converted to a hydroxyl radical (OH.) by reaction with iron ion ($Fe^{2+}$) or copper ion ($Cu^{1+}$) in cells (see the following chemical formula (2)).

$$Fe^{2+} + H_2O_2 \rightarrow Fe^{3+} + HO^- + HO. \tag{2}$$

$$Cu^{1+} + H_2O_2 \rightarrow Cu^{2+} + HO^- + HO. \tag{3}$$

The hydroxyl radical is known to have higher reactivity and higher oxidizing power than superoxide. The hydroxyl radical oxidizes lipids to form lipid radicals, lipid peroxyl radicals, and lipid peroxides through chain lipid peroxidation. Active oxygen causes the following problems.

1. Lipid peroxides: Water-insoluble lipids (cholesterol esters and neutral lipids) are transported in blood as lipoproteins after combination with apoproteins. The lipoproteins include low density lipoproteins (LDL), which contain lipids in an amount of 90%. Therefore, after oxidization, the low density lipoproteins contain the largest amount of lipid peroxides. The formation of oxidized LDLs may cause arteriosclerosis.

2. Reduction in enzymatic activity: If enzyme proteins are oxidized and modified, the enzymatic activity decreases, and the function of cells decreases.

3. Occurrence of arteriosclerosis, myocardial infarction, and cerebral infarction: Oxidized LDLs may damage vascular endothelial cells, causing arteriosclerosis and thrombotic diathesis.

4. Carcinogenesis: All active oxygen species damage nucleic acids. If DNA is oxidized and damaged, the cells become cancerous or die.

5. Acceleration of aging.

6. Reduction in life.

7. Cataract.

8. Blotches on skin.

9. Alzheimer's disease.

10. Kidney disease.

11. Redox regulation: Active oxygen finally affects insulin secretion inhibition, and this may cause diabetes and the like.

As described above, active oxygen adversely affects the human body. Therefore, it is important to scavenge such active oxygen. Generally, hydrogen molecules are harmless to the human body and have reducing properties. Therefore, hydrogen molecules are considered to be suitable for scavenging active oxygen.

However, as described above, it is known that hydrogen molecules have a slow reaction rate, do not react with oxidizing substances such as hypochlorous acid, and cannot directly reduce active oxygen. If hydrogen molecules can be activated to react with active oxygen, anti-active oxygen measures highly safe for the human body can be obtained. Moreover, to practically use hydrogen molecules as the anti-active oxygen measures, the life thereof is an important factor.

If hydrogen molecules can be activated to react with active oxygen, anti-active oxygen measures highly safe for the human body can be obtained. Moreover, to practically use hydrogen molecules as the anti-active oxygen measures, the life thereof is an important factor.

The problems to be solved by the invention relate to a method for activating hydrogen molecules dissolved in water and stabilizing the concentration of the hydrogen molecules.

BRIEF SUMMARY OF THE INVENTION

The inventor has found that the above problems can be solved by allowing hydrogen molecules and hydrogen ions to coexist in water. Thus, the invention has been completed. Hereinafter, the present invention is described.

(1) A method for activating and stabilizing hydrogen molecules dissolved in water, characterized by allowing hydrogen ions to coexist with the hydrogen molecules.

(2) The method for activating and stabilizing hydrogen molecules dissolved in water according to the paragraph (1), characterized by dissolving and dissociating an organic acid in water to produce the hydrogen ions.

(3) The method for activating and stabilizing hydrogen molecules dissolved in water according to the paragraph (1), characterized by dissolving and dissociating carbon dioxide gas in water to produce the hydrogen ions.

(4) The method for activating and stabilizing hydrogen molecules dissolved in water according to the paragraph (1), characterized by blowing hydrogen gas into water to dissolve the hydrogen molecules in the water.

(5) The method for activating and stabilizing hydrogen molecules dissolved in water according to the paragraph (1), characterized by cathodically electrolyzing an acidic aqueous solution containing an organic acid dissolved therein and thereby producing the hydrogen molecules to allow the hydrogen molecules and the hydrogen ions to coexist.

(6) The method for activating and stabilizing hydrogen molecules dissolved in water according to the paragraph (1), characterized by, using a three-chamber type electrolytic cell including an anode chamber, a cathode chamber, and an intermediate chamber provided between the anode and cathode chambers, supplying to the intermediate chamber an acidic aqueous solution containing an organic acid dissolved therein and thereby producing the hydrogen molecules to allow the hydrogen ions to coexist with the hydrogen molecules.

(7) The method for activating and stabilizing hydrogen molecules dissolved in water according to any one of the paragraphs (1) to (6), characterized by degassing the water and allowing the hydrogen molecules and the hydrogen ions to coexist.

(8) The method for activating and stabilizing hydrogen molecules dissolved in water according to anyone of the paragraphs (1) to (7), characterized in that a concentration of the hydrogen molecules is 0.1 ppm or more.

(9) The method for activating and stabilizing hydrogen molecules dissolved in water according to anyone of the paragraphs (1) to (8), characterized in that a concentration of the hydrogen ions is $10^{-7}$ M or more.

(10) A storage container for active hydrogen molecule-dissolved water, characterized in that the container is a pressure-resistant container filled with hydrogen gas, carbon dioxide gas, and water in which hydrogen molecules and hydrogen ions are allowed to coexist.

(11) A storage container for active hydrogen molecule-dissolved water, characterized in that the container is h pressure-resistant container filled with hydrogen gas, nitrogen gas, and water in which hydrogen molecules and hydrogen ions are allowed to coexist.

(12) An apparatus for supplying active hydrogen molecule-dissolved water, comprising: a pressure-resistant water tank containing water in which hydrogen molecules and hydrogen ions are allowed to coexist; a pipe; a gas cylinder for pressure-injecting hydrogen gas and carbon dioxide gas or hydrogen gas and nitrogen gas into the water tank through the pipe; and a supply pipe for supplying, from the water tank, the water in which hydrogen molecules and hydrogen ions are allowed to coexist.

(13) An active oxygen scavenger, comprising water in which hydrogen molecules and hydrogen ions are allowed to coexist.

(14) A hypotensive drug, comprising water in which hydrogen molecules and hydrogen ions are allowed to coexist.

(15) The hypotensive drug according to the paragraph (14), further comprising an essential trace element dissolved therein, selected from the group consisting of iron, zinc, copper, and manganese.

(16) A hypoglycemic drug, comprising water in which hydrogen molecules and hydrogen ions are allowed to coexist.

(17) The hypoglycemic drug according to the paragraph (16), further comprising an essential trace element dissolved therein, selected from the group consisting of iron, zinc, copper, and manganese.

(18) A skin conditioner, comprising water in which hydrogen molecules and hydrogen ions are allowed to coexist.

(19) The skin-conditioner according to the paragraph (18), further comprising an essential trace element dissolved therein, selected from the group consisting of iron, zinc, copper, and manganese.

(20) An anti-obesity drug, comprising water in which hydrogen molecules and hydrogen ions are allowed to coexist.

(21) The anti-obesity drug according to the paragraph (20), further comprising an essential trace element dissolved therein, selected from the group consisting of iron, zinc, copper, and manganese.

According to the present invention, hydrogen molecules dissolved in water can be activated and stabilized. Therefore, the invention can provide water containing activated hydrogen molecules dissolved therein, having the ability to scavenge active oxygen in the long term.

BRIEF DESCRIPTION OF THE DRAWINGS

FIG. 1 is a diagram describing activation energy.

FIG. 2 is a diagram describing complexes of a hydrogen ion and hydrogen molecule(s).

FIG. 3 is a structural drawing of a two-chamber type electrolytic cell.

FIG. 4 is a structural drawing of a three-chamber type electrolytic cell.

FIG. 5 shows the effect of hydrogen ions on the concentration of dissolved hydrogen.

FIG. 6 is a set of graphs showing ultraviolet-visible absorption spectra of DPPH.

FIG. 7 shows the flows in a system using the two-chamber type electrolytic cell.

FIG. 8 shows the flows in a system using the three-chamber type electrolytic cell.

FIG. 9 shows a dispensing system for active hydrogen molecule-dissolved water.

FIG. 10 shows a structure of three-chamber type electrolytic cell utilizing fluorine-based cation exchange membranes and reaction scheme.

FIG. 11 shows a microstructure in fluorine-based cation exchange membrane.

FIG. 12 shows an arrangement in a cluster form of exchange groups in fluorine-based cation exchange membrane.

FIG. 13 shows a formation of cluster ions.

FIG. 14 shows an arrangement of hydrogen ion clusters in ion exchange membrane.

FIG. 15 shows rate of absorption of water in fluorine-based cation exchange membrane.

FIG. 16 shows a basic electrolytic cell structure utilizing fluorine-based ion exchange membrane.

FIG. 17 shows a structure of three-chamber type electrolytic cell utilizing vinyl chloride-based and hydrocarbon-based cation exchange membranes and reaction scheme.

FIG. 18 shows a structure of three-chamber type electrolytic cell utilizing cation exchange membrane or anion exchange membrane of vinyl chloride-based and hydrocarbon-based and reaction scheme.

The description of the reference numerals is as follows:
31 anode chamber
39 cathode chamber
41 anode chamber
49 cathode chamber
51 intermediate chamber
75 cathode chamber
76 anode chamber
86 cathode chamber
87 intermediate chamber
88 anode chamber

DETAILED DESCRIPTION OF THE INVENTION

To solve the current problems with hydrogen molecules, the following method has been devised. First, a method for extending the life of the solubility of hydrogen molecules has been developed. In the presence of hydrogen ions in water containing hydrogen molecules dissolved therein, it is presumed that weak complexes of hydrogen molecules and hydrogen ions constituted by hydrogen atoms are formed, as shown in FIG. 2, so that the dissolved hydrogen molecules are stabilized in water. One example of the complexes is a type-A complex of molecular hydrogen and a hydrogen ion shown in FIG. 2, and another example is a type-B complex of hydrogen in fine gas bubble form (n hydrogen molecules) and a hydrogen ion.

The formation of complexes of hydrogen ions and hydrogen molecules may reduce the activation energy, as shown in FIG. 1. Therefore, the hydrogen molecules may be activated to scavenge active oxygen. Representative active oxygen species include a superoxide radical. However, 1,1-Diphenyl-2-picrylhydrazyl (DPPH), which is a metastable free radical, is used for evaluation tests. DPPH was used to evaluate the activity of hydrogen molecules. The results showed that the coexistence of hydrogen ions and hydrogen molecules allows DPPH reduction to occur.

In potable water containing the hydrogen complexes, the pH must be in the range of 2.5 to 7. If possible, the pH is desirably 3.5 or more.

To obtain the effects of hydrogen molecules in water, the concentration of hydrogen molecules is preferably 0.1 ppm or more, and the concentration of hydrogen ions is preferably $10^{-7}$ M of more.

To allow hydrogen ions to exist in water, a method may be used in which an organic acid having buffering properties is dissolved and dissociated in water to produce hydrogen ions.

When an organic acid having buffering properties is used, a large amount of hydrogen ions can be supplied by increasing the acid concentration in a weakly acidic pH range. In consideration of safety to the human body, it is desirable to use the following organic acids classified as food carbon hydrates. Examples of such organic acids include ascorbic acid, lactic acid, malic acid, citric acid, succinic acid, fumaric acid, acetic acid, malonic acid, glutaric acid, adipic acid, and amino acid. These organic acids may be used alone or in combination of two or more.

Alternatively, hydrogen ions may be produced by dissolving and dissociating carbon dioxide gas in water.

No particular limitation is imposed on the method for allowing hydrogen molecules to be contained in water. Examples include a method in which hydrogen gas is allowed to be dissolved in water and a method in which water is electrolyzed to generate hydrogen molecules at the cathode.

When the method in which hydrogen gas is allowed to be dissolved in water is used, hydrogen gas may be blown into water.

When the method in which hydrogen molecules to be dissolved are produced by the electrolytic method is used, an acidic aqueous solution containing an organic acid dissolved therein is electrolyzed, whereby active hydrogen molecule-dissolved water in which hydrogen molecules and hydrogen ions are allowed to coexist can be produced in a single step.

When the electrolytic method is used, for example, hydrogen ions and hydrogen molecules can be produced by supplying an aqueous solution of an organic acid or the like to a cathode chamber 31 of a two-chamber type electrolytic cell shown in FIG. 3. In this electrolytic cell, the electrolytic cell is separated by a separation membrane 35. In another method, hydrogen ions and hydrogen molecules are dissolved in a cathode solution by supplying an organic acid or the like to an intermediate chamber 51 of a three-chamber type electrolytic cell shown in FIG. 4. In this electrolytic cell, the intermediate chamber 51 is disposed between an anode chamber 41 and a cathode chamber 49.

The object of the hydrogen-dissolved water in the present invention is to scavenge active oxygen, and it is desirable that water do not contain dissolved oxygen. To increase the solubility of hydrogen molecules, water is degassed to remove dissolved gases (air components such as oxygen and nitrogen), whereby the concentration of dissolved hydrogen can be increased. Therefore, preferably, the water used in the method of the present invention is degassed. Preferably, the water is degassed such that the dissolved oxygen concentration is 5 ppm or less.

When the active hydrogen molecule-dissolved water of the present invention is stored, the active hydrogen molecule-dissolved water, together with hydrogen gas, may be filled into a pressure-resistant container made of glass, an aluminum alloy, an iron alloy, or the like, in order to prevent a reduction in the concentration of hydrogen molecules. However, since hydrogen gas is explosive, it is preferable to use carbon dioxide gas or nitrogen gas together with hydrogen gas so that the concentration of hydrogen gas is reduced to its explosion limit (4%) or less.

As an apparatus for supplying the active hydrogen molecule-dissolved water of the present invention, an active hydrogen-dissolved water supply apparatus may be used which includes: a pressure-resistant water tank containing water in which hydrogen molecules and hydrogen ions are allowed to coexist; a pipe; a gas cylinder for pressure-injecting carbon dioxide gas or nitrogen gas into the water tank through the pipe; and a supply pipe for supplying, from the water tank, the water in which hydrogen molecules and hydrogen ions are allowed to coexist. The supply pipe of the supply apparatus may include an electromagnetic valve so that the active hydrogen molecule-dissolved water can be dispensed.

The active hydrogen molecule-dissolved water of the present invention is excellent in the ability to scavenge active oxygen and therefore is expected to be used in applications such as an active oxygen scavenger, a hypotensive drug, a hypoglycemic drug, a skin conditioner, and an anti-obesity drug. Moreover, the addition of a trace element such as iron, zinc, copper, or manganese is expected to improve the active oxygen scavenging effect, the hypotensive effect, the hypoglycemic effect, and the anti-obesity effect. Iron, zinc, and copper are known to activate an enzyme having an active oxygen scavenging function. In addition, it has been reported that manganese has an effect of inhibiting arteriosclerosis.

Hereinafter, the present invention will be described by way of Examples, but the invention is not limited to the Examples.

Example 1

First, 1.0 mg of lactic acid was dissolved in 2,000 ml of pure water which had been degassed to have a dissolved oxygen concentration of 1 ppm. For comparison purposes, weak alkaline degassed water having a pH of 8.5 adjusted with sodium hydroxide was used. Hydrogen gas was dissolved in these two kinds of water, and the temporal changes in the dissolved hydrogen concentration were measured. A PET bottle and a glass bottle were used as a container. The results are shown in FIG. 5. As is clear from the figure, the life of the weak alkaline hydrogen molecule-dissolved water stored in the PET bottle was about 3 days. However, the life of the hydrogen molecule-dissolved water including lactic acid coexisting with hydrogen molecules was extended to about 5 months. These results show that hydrogen ions stabilize dissolved hydrogen molecules. In addition, the results suggest the interaction between hydrogen ions and hydrogen molecules (the formation of complexes).

Example 2

A DPPH solution was added to the activated hydrogen molecule-dissolved water prepared in Example 1, and the degree of DPPH free radical scavenging activity was measured based on changes in ultraviolet-visible absorption spectra. First, a 1 mM ethanol solution of DPPH was prepared, and 0.25 ml of the prepared solution was mixed with 5 ml of each sample. Subsequently, UV-VIS measurement was performed (Shimadzu Multi Spec 1500 (product name), a 1 cm quartz cell was used, reference: pure water), and the peak intensities at 551 nm were compared (the comparison was made with the results of a specimen prepared in the same manner as the Example except that the same amount of pure water was added in place of the sample, and the peak intensity of this sample was set to 1).

The results are shown in FIG. 6. As can be seen, when the solution in which lactic acid and the water dissolving hydrogen molecules was compared with pure water, the absorbance of DPPH was lower in the solution containing lactic acid and hydrogen molecules dissolved therein than in pure water. The results show that the coexistence of hydrogen molecules with hydrogen ions improves the reduction function (the ability to scavenge active oxygen).

Example 3

To allow hydrogen ions and hydrogen molecules to coexist, the two-chamber type electrolytic cell shown in FIG. 3 was used which includes an anode chamber 31 and the cathode chamber 39. In the two-chamber type electrolytic cell, porous anode and cathode electrodes each made of a platinum-plated titanium plate having an area of 48 $cm^2$ were disposed on opposite sides of a fluorine-based cation exchange membrane so as to be in proximity to each other. As in Example 1, an organic acid was used as a supply source of hydrogen ions, and a lactic acid-dissolved solution prepared as in Example 1 was supplied at about 0.5 L/min to the cathode chamber 75 and the anode chamber 76 of the electrolytic cell in the manner shown in the flows in the system in FIG. 7. Cathodic water having a pH of about 3.97 and a dissolved hydrogen concentration of 0.88 ppm was produced.

Example 4

To allow hydrogen ions and hydrogen molecules to coexist, the three-chamber type electrolytic cell was used. As shown in FIG. 4, in the three-chamber type electrolytic cell, the intermediate chamber 51 partitioned by fluorine-based cation exchange membranes is provided between the anode chamber 41 and the cathode chamber 49. The intermediate chamber 51 was filled with a cation exchange resin. Porous anode and cathode electrodes each made of a platinum-plated titanium plate having an area of 48 $cm^2$ were brought into intimate contact with the respective separation membranes. As shown in the flows in the system in FIG. 8, a 1M aqueous lactic acid solution was supplied to the intermediate chamber 87. A lactic acid-containing solution prepared as in Example 1 was supplied at about 0.5 L/min to the cathode chamber 86 and the anode chamber 88 of the electrolytic cell. Cathodic water having a pH of about 4.25 and a dissolved hydrogen concentration of 0.96 ppm was produced.

Example 5

A 1M aqueous citric acid solution was supplied to the intermediate chamber 87 in the same manner as shown in the flows in the system in FIG. 8, as in Example 4. A solution was supplied in the same manner as in Example 1 at about 0.5 L/min to the cathode chamber 86 and the anode chamber 88 of the electrolytic cell. Cathodic water having a pH of about 4.8 and a dissolved hydrogen concentration of 0.92 ppm was produced. The concentration of citric acid in the cathodic water was measured and was $5.2 \times 10^{-6}$ M. The results show that the hydrogen ion concentration is greater than the anion concentration.

Example 6

Data for decrease in blood pressure was collected using the activated hydrogen molecule-dissolved water produced in Example 4. The blood pressure of subjects was measured before intake and after intake for 3 months. The results are shown in Table 1. The daily intake was basically 250 ml in the morning after fasting and 250 ml before bedtime. As is clear from the table, a decrease in blood pressure was observed after three months intake of the water in which hydrogen ions coexist with hydrogen molecules. These results show the effects of the present invention.

TABLE 1

Relation between blood pressure and water in which hydrogen ions coexist with hydrogen molecules

| Sex | Age | Before intake (mmHg) | After intake (mmHg) |
|---|---|---|---|
| Male | 45 | 145 | 124 |
| Male | 48 | 156 | 134 |
| Female | 50 | 169 | 137 |
| Male | 51 | 164 | 130 |
| Female | 51 | 151 | 143 |
| Female | 53 | 159 | 147 |
| Male | 58 | 165 | 139 |
| Female | 62 | 157 | 128 |
| Female | 62 | 164 | 134 |
| Male | 65 | 163 | 151 |

Example 7

Data for decrease in blood sugar level was collected using the activated hydrogen molecule-dissolved water produced in Example 4. The measured blood sugar levels before intake and after intake for 3 months are shown in Table 2. The daily intake was basically 250 ml in the morning after fasting and 250 ml before bedtime. As is clear from the table, a decrease in blood sugar level was observed after three months intake of the water in which hydrogen ions coexist with hydrogen molecules. These results show the effects of the present invention.

TABLE 2

Relation between blood pressure and water in which hydrogen ions coexist with hydrogen molecules

| Sex | Before intake (mg/dl) | After intake (mg/dl) |
| --- | --- | --- |
| Male | 130 | 102 |
| Female | 195 | 154 |
| Female | 154 | 121 |
| Female | 132 | 104 |
| Male | 129 | 98 |
| Male | 138 | 105 |
| Female | 149 | 112 |
| Male | 165 | 128 |
| Male | 155 | 119 |
| Female | 147 | 132 |

Example 8

Data for effects on lightness of skin was collected using the activated hydrogen molecule-dissolved water produced in Example 4. First, a face was exposed to the vapor of the active hydrogen molecule-dissolved water for about 5 minutes. A facial treatment apparatus (steamer, product of HOMEO-STYLE, Inc.) was used as an apparatus for generating the vapor. A skin checker (product of JAPAN GALS Co., Ltd.) was used as a sensor for measuring the lightness of skin. Water treated with a reverse osmosis membrane, alkaline hydrogen-dissolved water, and weakly acidic hydrogen-dissolved water were used as the raw water for the vapor, and the results were compared with each other. The alkaline hydrogen-dissolved and existing water was produced by supplying saturated brine to the intermediate chamber of the three-chamber type electrolytic cell shown in FIG. 4. In this case, alkaline hydrogen-dissolved water having a pH of 11.7 and a dissolved hydrogen concentration of 1.02 ppm was obtained. The water prepared in Example 4 was used as the weakly acidic hydrogen-dissolved water. The effects of these waters were evaluated in 30 subjects. The results are shown in Table 3. In Table 3, "RO water" represents the water treated with a reverse osmosis membrane; "Electrolyzed water 1" represents the alkaline hydrogen-dissolved water; and "Electrolyzed water 2" represents the weakly acidic hydrogen-dissolved water. The results for untreated skin were also shown in the table for comparison. As is clear from the table, the lightness of skin was most improved when the weakly acidic hydrogen-dissolved water was used.

[Table 3]

TABLE 3

Relation between lightness of skin and various waters

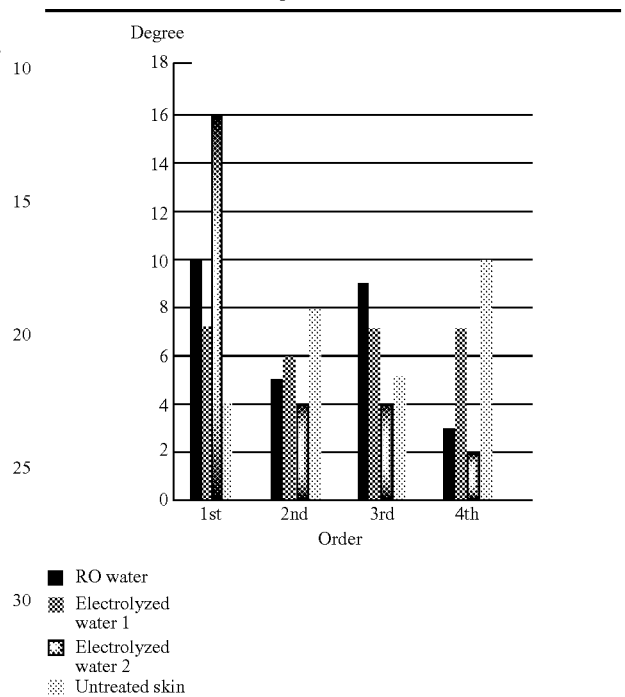

■ RO water
▩ Electrolyzed water 1
▨ Electrolyzed water 2
▧ Untreated skin

Example 9

Data for reduction in weight was collected using the activated hydrogen molecule-dissolved water produced in Example 4. The measured weights of subjects before intake and after intake for 3 months are shown in Table 4. The daily intake was basically 250 ml in the morning after fasting and 250 ml before bedtime. As is clear from the table, a decrease in weight was observed after three months intake of the water in which hydrogen ions coexist with hydrogen molecules. These results show the effects of the present invention.

[Table 4]

TABLE 4

Effects of water in which hydrogen ions coexist with hydrogen molecules on changes in body weight

| Sex | Age | Before intake (kg) | After intake (kg) |
| --- | --- | --- | --- |
| Male | 32 | 65 | 63 |
| Female | 35 | 55 | 51 |
| Female | 38 | 58 | 55 |
| Male | 40 | 12 | 71 |
| Male | 41 | 80 | 75 |
| Female | 45 | 60 | 59 |
| Female | 49 | 63 | 60 |
| Male | 50 | 85 | 81 |
| Male | 52 | 79 | 71 |
| Female | 55 | 85 | 79 |

Example 10

To sell the active hydrogen molecule-dissolved water produced in Example 4 in a bottled form, it is desirable to further extend the life of the dissolved hydrogen. To this end, a dispensing system shown in FIG. 9 was devised. The active hydrogen molecule-dissolved water was charged into a water tank 92 made of a metal such as aluminum so that the volatilization of hydrogen molecules is prevented. The water tank 92 was pressurized by pressurized hydrogen and carbon dioxide gases or pressurized hydrogen and nitrogen gases stored in a gas cylinder 91 through a pipe 96, and the active hydrogen molecule-dissolved water was supplied through supply pipes provided with electromagnetic valves. Cooled or heated active hydrogen molecule-dissolved water may be supplied to a point of use by using a cooler or a heater.

The active hydrogen molecule-dissolved water obtained by the method of the present invention is useful as an active oxygen scavenger, a hypotensive drug, a hypoglycemic drug, a skin conditioner, and an anti-obesity drug.

The invention claimed is:

1. A method for activating and stabilizing hydrogen molecules dissolved in water, comprising:
   supplying an organic acid into an intermediate chamber of a three-chamber electrolytic cell including an anode chamber, a cathode chamber, and the intermediate chamber present between the anode chamber and the cathode chamber formed with a fluorine-based cation exchange membrane and filled with a cation exchange resin; and
   obtaining cathodic water coexisting hydrogen ions and the hydrogen molecules in the water,
   wherein a concentration of the hydrogen molecules is 0.1 to 0.96 ppm, and
   a concentration of the hydrogen ions is $1 \times 10^{-7}$ to $3 \times 10^{-3}$ M.

2. The method for activating and stabilizing hydrogen molecules dissolved in water according to claim 1, wherein the obtaining of the cathodic water includes cathodically electrolyzing an acidic aqueous solution containing the organic acid dissolved therein and thereby producing the hydrogen molecules which coexist with the hydrogen ions.

3. A storage container for active hydrogen molecule-dissolved water, containing hydrogen ions in a concentration of $1 \times 10^{-7}$ to $3 \times 10^{-3}$ M and hydrogen molecules in a concentration of 0.1 to 0.96 ppm obtained by supplying an organic acid into an intermediate chamber of a three-chamber electrolytic cell including an anode chamber, a cathode chamber, and the intermediate chamber present between the anode chamber and the cathode chamber formed with a fluorine-based cation exchange membrane and filled with a cation exchange resin,
   wherein the container is a pressure-resistant container filled with hydrogen gas, carbon dioxide gas, and water in which the hydrogen molecules and the hydrogen ions coexist.

4. A storage container for active hydrogen molecule-dissolved water, containing hydrogen ions in a concentration of $1 \times 10^{-7}$ to $3 \times 10^{-3}$ M and hydrogen molecules in a concentration of 0.1 to 0.96 ppm obtained by supplying an organic acid into an intermediate chamber of a three-chamber electrolytic cell including an anode chamber, a cathode chamber, and the intermediate chamber present between the anode chamber and the cathode chamber formed with a fluorine-based cation exchange membrane and filled with a cation exchange resin,
   wherein the container is a pressure-resistant container filled with hydrogen gas, nitrogen gas, and water in which the hydrogen molecules and the hydrogen ions coexist.

5. An apparatus for supplying active hydrogen molecule-dissolved water, comprising:
   a pressure-resistant water tank containing water in which hydrogen molecules in a concentration of 0.1 to 0.96 ppm and hydrogen ions in a concentration of $1 \times 10^{-7}$ to $3 \times 10^{-3}$ M coexist obtained by supplying an organic acid into an intermediate chamber of a three-chamber electrolytic cell including an anode chamber, a cathode chamber, and the intermediate chamber present between the anode chamber and the cathode chamber formed with a fluorine-based cation exchange membrane and filled with a cation exchange resin;
   a pipe;
   a gas cylinder for pressure-injecting hydrogen gas and carbon dioxide gas or hydrogen gas and nitrogen gas into the water tank through the pipe; and
   a supply pipe for supplying, from the water tank, the water in which the hydrogen molecules and the hydrogen ions coexist.

6. An active oxygen remover scavenger, comprising:
   water;
   hydrogen molecules in a concentration of 0.1 to 0.96 ppm; and
   hydrogen ions in a concentration of $1 \times 10^{-7}$ to $3 \times 10^{-3}$ M,
   wherein the hydrogen molecules and the hydrogen ions coexist in the water obtained by supplying an organic acid into an intermediate chamber of a three-chamber electrolytic cell including an anode chamber, a cathode chamber, and the intermediate chamber present between the anode chamber and the cathode chamber formed with a fluorine-based cation exchange membrane and filled with a cation exchange resin.

7. The method for activating and stabilizing hydrogen molecules dissolved in water according to claim 1, wherein
   the anode chamber has an anode electrode,
   the cathode chamber has a cathode electrode, and
   the anode electrode and the cathode electrode are made of a platinum-plated titanium plate.

8. The method for activating and stabilizing hydrogen molecules dissolved in water according to claim 7, wherein the platinum-plate titanium plate has an area of 48 $cm^2$.

9. The storage container for active hydrogen molecule-dissolved water according to claim 3, wherein
   the anode chamber has an anode electrode,
   the cathode chamber has a cathode electrode, and
   the anode electrode and the cathode electrode are made of a platinum-plated titanium plate.

10. The storage container for active hydrogen molecule-dissolved water according to claim 9, wherein the platinum-plate titanium plate has an area of 48 $cm^2$.

11. The storage container for active hydrogen molecule-dissolved water according to claim 4, wherein
    the anode chamber has an anode electrode,
    the cathode chamber has a cathode electrode, and
    the anode electrode and the cathode electrode are made of a platinum-plated titanium plate.

12. The storage container for active hydrogen molecule-dissolved water according to claim 11, wherein the platinum-plate titanium plate has an area of 48 $cm^2$.

13. The apparatus for supplying active hydrogen molecule-dissolved water according to claim 5, wherein
    the anode chamber has an anode electrode,
    the cathode chamber has a cathode electrode, and the anode electrode and the cathode electrode are made of a platinum-plated titanium plate.

14. The apparatus for supplying active hydrogen molecule-dissolved water according to claim 13, wherein the platinum-plate titanium plate has an area of 48 cm$^2$.

15. The active oxygen scavenger according to claim 6, wherein the anode chamber has an anode electrode, the cathode chamber has a cathode electrode, and the anode electrode and the cathode electrode are made of a platinum-plated titanium plate.

16. The active oxygen scavenger according to claim 15, wherein the platinum-plate titanium plate has an area of 48 cm$^2$.

* * * * *